US008399197B2

(12) United States Patent
Behlke et al.

(10) Patent No.: US 8,399,197 B2
(45) Date of Patent: *Mar. 19, 2013

(54) METHODS FOR AMPLIFYING POLYMERIC NUCLEIC ACIDS

(75) Inventors: Mark Aaron Behlke, Coralville, IA (US); Joseph Alan Walder, Chicago, IL (US); Jeffrey A. Manthey, Iowa City, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/555,967

(22) Filed: Sep. 9, 2009

(65) Prior Publication Data
US 2010/0075383 A1    Mar. 25, 2010

Related U.S. Application Data

(63) Continuation of application No. 10/911,652, filed on Aug. 2, 2004, now Pat. No. 7,629,152, which is a continuation-in-part of application No. 10/377,168, filed on Feb. 28, 2003, now Pat. No. 7,112,406.

(60) Provisional application No. 60/360,995, filed on Mar. 1, 2002, provisional application No. 60/492,120, filed on Aug. 1, 2003.

(51) Int. Cl.
C12Q 1/68      (2006.01)
C07H 21/04    (2006.01)

(52) U.S. Cl. .................................. 435/6.12; 536/24.33

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 4,957,858 A | 9/1990 | Chu et al. | |
| 5,219,727 A | 6/1993 | Wang et al. | |
| 5,422,252 A | 6/1995 | Walker et al. | |
| 5,455,166 A | 10/1995 | Walker | |
| 5,683,896 A | 11/1997 | Hartley et al. | |
| 5,824,517 A | 10/1998 | Cleuziat et al. | |
| 5,998,583 A | 12/1999 | Korsmeyer | |
| 6,027,923 A | 2/2000 | Wallace | |
| 6,124,120 A | 9/2000 | Lizardi | |
| 6,214,587 B1 | 4/2001 | Dattagupta et al. | |
| 6,251,639 B1 | 6/2001 | Kurn | |
| 6,335,184 B1 | 1/2002 | Reyes et al. | |
| 7,221,406 B2 | 5/2007 | Yamashita | |
| 2001/0024812 A1* | 9/2001 | Guegler et al. | 435/91.5 |
| 2001/0044145 A1* | 11/2001 | Monia et al. | 435/199 |
| 2002/0004228 A1* | 1/2002 | Holloway | 435/69.6 |
| 2002/0072095 A1 | 6/2002 | Hartley et al. | |
| 2003/0186384 A1* | 10/2003 | Barth et al. | 435/69.5 |
| 2003/0228596 A1 | 12/2003 | Liu et al. | |

FOREIGN PATENT DOCUMENTS

| | | |
|---|---|---|
| EP | 0416817 A2 | 3/1991 |
| WO | 01/64952 | 9/2001 |
| WO | 03/074724 | 9/2003 |

OTHER PUBLICATIONS

Eritja et al., Synthesis of Oligonucleotides Containing the Abasic Site Model Compound 1,4-Anhydro-2-Deoxy-D-Ribitol, Nucleosides & Nucleotides, vol. 6. No. 4, 803-814, (1987).
Kwok and Higuchi, Avoiding false positives with PCR, Nature, vol. 339, May 1989, 237-238.
Saiki et al., Enzymatic Amplification of B-Globin Genomic Sequences and Restriction Site Analysis for Diagnosis of Sickle Cell Anemia, Science, vol. 230, 1350-1354, (1985).
Newton et al., Analysis of any point mutation in DNA. The amplification refractory mutation system (ARMS), Nucleic Acid Research, vol. 17, No. 7, 1989, 2504-2516.
Seela et al., Oligodeoxyribonucleotides containing 1,3-propanediol as nucleoside substitute, Nucleic Acids Research, vol. 15, No. 7, 1987, 3113-3129.
Longo et al., Use of uracil DNA glycosylase to control carry-over contamination in polymerase chain reactions, Gene, 93(1); 1990, 125-128.
Ugozzoli and Wallace, Allele-Specific Polymerase Chain Reaction, Methods, vol. 2, No. 1, Feb. 1991, 42-48.
Reyes et al., Linked Linear Amplification: A New Method for the Amplification of DNA, Clinical Chemistry 2001, 47:1, 31-40.
Wu and Wallace, The Ligation Amplification Reaction (LAR)-Amplification of Specific DNA Sequences Using Sequential Rounds of Template-Dependent Ligation, Genomics, vol. 4, 1989, 560-569.
Newton et al., The Production fo PCR products with 5' single-stranded tails using primers that incorporate novel phosphoramidite intermediates, Nucleic Acids Research, vol. 21, No. 5, 1993, 1155-1162.
Gade et al., Incorporation of Nonbase Residues into Synthetic Oligonucleotides and Their Use in the PCR, Gata 10(2), 1993, 61-65.

(Continued)

Primary Examiner — Samuel Woolwine
(74) Attorney, Agent, or Firm — John A. Petravich

(57) ABSTRACT

The invention provides compositions and methods for amplifying nucleic acid polymer sequences in a high complexity nucleic acid sample. The unique compositions of the invention include a primer set composed of a mixture of two types of primers for DNA synthesis. For extension in one direction, the primers all contain modifications that destroy their ability to serve as templates that can be copied by DNA polymerases. For extension in the opposite direction the set includes at least one primer that can serve as a template and be replicated by DNA polymerases throughout its length. The method can be carried out by mixing the nucleic acid polymer sequence of interest with the set of DNA synthesis primers in an amplification reaction mixture. The reaction mixture is then subjected to temperature cycling analogous to the temperature cycling in PCR reactions. At least one primer in the primer set hybridizes to the nucleic acid polymer. It is preferred that the non-replicable primer hybridizes to the nucleic acid polymer and is extended to produce an extension product that contains sequence from the nucleic acid polymer to which the replicable primer then hybridizes. Of course, if the nucleic acid polymer is double stranded, both the replicable and nonreplicable primers will hybridize and be extended by DNA polymerase.

41 Claims, No Drawings

OTHER PUBLICATIONS

Walder et al., use of PCR primers containing a 3'-terminal ribose residue to prevent cross-contamination of amplified sequences, Nucleic Acids Research vol. 21, No. 18, 1993, 4339-4343.

Walker et al., Strand displacement amplification—an isothermal, in vitro DNA amplification technique, Nucleic Acids Research, vol. 20, No. 7, 1992, 1691-1966.

Garcia-Quintanilla et al., Single-Tube Balanced Heminested PCR for Detecting *Mycobacterium tuberculosis* in Smear-Negative Samples, Journal of Clinical Microbiology, vol. 38, No. 3, 2000, 1166-1169.

Little et al., Strand Displacement Amplification and Homogenous real-Time Detection Incorporated in a Second-Generation DNA Probe System, BDProbeTecET, Clinical Chemistry, 45:6, 1999, 777-784.

Nycz et al., Quantitative Reverse Transcription Strand Displacement Amplification: Quantitation of Nucleic Acids Using an Isothermal Amplification Technique, Analytical Biochemistry, 259, 1998, 226-234.

Lizardi et al., Mutation Detection and Single-Molecule Counting using Isothermal Rolling-Circle Amplification, Nature Genetics, vol. 19, 1998, 225-232.

Poddar, Symmetric vs Asymmetric PCR and Molecular Beacon Probe in the Detection of a Target Gene of Adenovirus, Molecular and Cellular Probes, 14, 2000, 25-32.

Stump M D et al., "The Use of Modified Primers to Eliminate Cycle Sequencing Artifacts", Nucleic Acids Research, Oxford University Press, Surrey, GB, vol. 27, No. 23, pp. 4642-4648 (1999).

Edwards et al., Multiplex PCT: Advantages, Development, and Applications. (PCR Methods and Applications 3:S65-S73, 1994).

* cited by examiner

SEQUENCE LISTING

```
<160> NUMBER OF SEQ ID NOS: 77

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgactcact atagacatgg tcaac                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: Nitroindole
```

```
<400> SEQUENCE: 2
acgactcact atagacatng tcaac                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(19)
<223> OTHER INFORMATION: Nitroindole

<400> SEQUENCE: 3
acgactcact atagacanng tcaac                                           25

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgactcact atagacat                                                   18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgactcact atagaca                                                    17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: Nitroindole

<400> SEQUENCE: 6
acgactcact atagacan                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: Nitroindole

<400> SEQUENCE: 7
```

```
acgactcact atagacnn                                                         18
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ccaccgtgtt cttcgacatc                                                       20
```

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ccaccgtgtt ct                                                               12
```

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: Nitroindole

<400> SEQUENCE: 10

```
ccaccgtgtt ctn                                                              13
```

<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(13)
<223> OTHER INFORMATION: Nitroindole

<400> SEQUENCE: 11

```
ccaccgtgtt cnn                                                              13
```

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
atggcgagcc cttggg                                                           16
```

<210> SEQ ID NO 13
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
gatccacgtt atgtcggagt g                                                    21

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caaagttcca aagacagcag aaaac                                                25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cgcgtctgct tcgagctgtt tgc                                                  23

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccaccgtgtt ctt                                                             13

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccaccgtgtt ct                                                              12

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (11)..(11)
<223> OTHER INFORMATION: 2'-O-Methyl guanine
<220> FEATURE:
<221> NAME/KEY: modified_base
<222> LOCATION: (12)..(12)
<223> OTHER INFORMATION: 2'-O-Methyl adenine
<220> FEATURE:
```

```
<221> NAME/KEY: modified_base
<222> LOCATION: (13)..(13)
<223> OTHER INFORMATION: 2'-O-Methyl uracil
<220> FEATURE:
<221> NAME/KEY: modified_base
<222> LOCATION: (14)..(14)
<223> OTHER INFORMATION: 2'-O-Methyl guanine
<220> FEATURE:
<221> NAME/KEY: modified_base
<222> LOCATION: (15)..(15)
<223> OTHER INFORMATION: 2'-O-Methyl cytosine
<220> FEATURE:
<221> NAME/KEY: modified_base
<222> LOCATION: (16)..(16)
<223> OTHER INFORMATION: 2'-O-Methyl adenine

<400> SEQUENCE: 18
ggatcctcta gaugcatgct cg                                          22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggatcctcta gatgcatgct cg                                          22

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatcctcta gatgc                                                  15

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggatcctcta gatg                                                   14

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(15)
<223> OTHER INFORMATION: Nitroindole

<400> SEQUENCE: 22
ggatcctcta gatgn                                                  15

<210> SEQ ID NO 23
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (11)..(11)
<223> OTHER INFORMATION: 2'-O-Methyl guanine
<220> FEATURE:
<221> NAME/KEY: modified_base
<222> LOCATION: (12)..(12)
<223> OTHER INFORMATION: 2'-O-Methyl adenine
<220> FEATURE:
<221> NAME/KEY: modified_base
<222> LOCATION: (13)..(13)
<223> OTHER INFORMATION: 2'-O-Methyl uracil
<220> FEATURE:
<221> NAME/KEY: modified_base
<222> LOCATION: (14)..(14)
<223> OTHER INFORMATION: 2'-O-Methyl guanine
<220> FEATURE:
<221> NAME/KEY: modified_base
<222> LOCATION: (15)..(15)
<223> OTHER INFORMATION: 2'-O-Methyl cytosine
<220> FEATURE:
<221> NAME/KEY: modified_base
<222> LOCATION: (16)..(16)
<223> OTHER INFORMATION: 2'-O-Methyl adenine

<400> SEQUENCE: 23
ggatcctcta gaugcatgct cg                                              22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (14)..(14)
<223> OTHER INFORMATION: 2'-O-Methyl guanine
<220> FEATURE:
<221> NAME/KEY: modified_base
<222> LOCATION: (15)..(15)
<223> OTHER INFORMATION: 2'-O-Methyl adenine
<220> FEATURE:
<221> NAME/KEY: modified_base
<222> LOCATION: (16)..(16)
<223> OTHER INFORMATION: 2'-O-Methyl cytosine
<220> FEATURE:
<221> NAME/KEY: modified_base
<222> LOCATION: (17)..(17)
<223> OTHER INFORMATION: 2'-O-Methyl adenine
<220> FEATURE:
<221> NAME/KEY: modified_base
<222> LOCATION: (18)..(18)
<223> OTHER INFORMATION: 2'-O-Methyl uracil
<220> FEATURE:
<221> NAME/KEY: modified_base
<222> LOCATION: (19)..(19)
<223> OTHER INFORMATION: 2'-O-Methyl guanine

<400> SEQUENCE: 24
acgactcact atagacaugg tcaac                                           25

<210> SEQ ID NO 25
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 25
ccaccgtgtt ctt                                                            13

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaccgtgtt ct                                                             12

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(10)
<223> OTHER INFORMATION: 2'-O-Methyl uracil
<220> FEATURE:
<221> NAME/KEY: modified_base
<222> LOCATION: (11)..(11)
<223> OTHER INFORMATION: 2'-O-Methyl cytosine
<220> FEATURE:
<221> NAME/KEY: modified_base
<222> LOCATION: (12)..(13)
<223> OTHER INFORMATION: 2'-O-Methyl uracil
<220> FEATURE:
<221> NAME/KEY: modified_base
<222> LOCATION: (14)..(14)
<223> OTHER INFORMATION: 2'-O-Methyl cytosine

<400> SEQUENCE: 27
ccaccgtguu cuucgacatc                                                     20

<210> SEQ ID NO 28
<211> LENGTH: 532
<212> TYPE: DNA
<213> ORGANISM: Homo sapiens

<400> SEQUENCE: 28
cccaatgagc tcatcaacaa aggctcagta ccatcagtga aatgtaaccg tctctcttcc         60
attcactaga tgagtttatc aaattaagta gccactccct taggatagtg gttaagtacc        120
tgcattttag tgctagacat cctgggttta aatcccacct acaccacttc tttttttgatc       180 tcgagcaaat tagtcccaat ctcctcattg gtaaaatggg cctaaaagag tacccgtgcc        240
atcgagcata agaatctaaa ttgtgatggg tgtaagcagg ctcctattca catccaccat        300
ccatctcctt gtggcatggg tcctgggcca ttaagtcagc caccagtccc ccattacctc        360
cccacactct gcttgctggg aagacccacc actctctgca tgcctaaaac acttgcacag       420
tacttgatat ggtttggctg tgtccccacc caaatctctt gaattcccac gtgttgtggg       480
agcgacccag tggaaggtaa ttgaatccca tcctgttctc attacagtaa at               532
```

```
<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caacaaaggc tcagtaccat cagtg                                              25

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caacaaaggc tcagtacc                                                      18

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caacaaaggc tcagtac                                                       17

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(19)
<223> OTHER INFORMATION: Nitroindole

<400> SEQUENCE: 32
caacaaaggc tcagtacnnt cagtg                                              25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (14)..(14)
<223> OTHER INFORMATION: 2'-O-Methyl guanine
<220> FEATURE:
<221> NAME/KEY: modified_base
<222> LOCATION: (15)..(15)
<223> OTHER INFORMATION: 2'-O-Methyl uracil
<220> FEATURE:
<221> NAME/KEY: modified_base
<222> LOCATION: (16)..(16)
<223> OTHER INFORMATION: 2'-O-Methyl adenine
<220> FEATURE:
```

```
<221> NAME/KEY: modified_base
<222> LOCATION: (17)..(18)
<223> OTHER INFORMATION: 2'-O-Methyl cytosine
<220> FEATURE:
<221> NAME/KEY: modified_base
<222> LOCATION: (19)..(19)
<223> OTHER INFORMATION: 2'-O-Methyl adenine

<400> SEQUENCE: 33
caacaaaggc tcaguaccat cagtg                                            25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgtctctctt ccattcacta gatgag                                           26

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtctctctt ccattcact                                                   19

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgtctctctt ccattcac                                                    18

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: Nitroindole

<400> SEQUENCE: 37
cgtctctctt ccattcacnn gatgag                                           26

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
```

```
<221> NAME/KEY: modified_base
<222> LOCATION: (15)..(15)
<223> OTHER INFORMATION: 2'-O-Methyl uracil
<220> FEATURE:
<221> NAME/KEY: modified_base
<222> LOCATION: (16)..(16)
<223> OTHER INFORMATION: 2'-O-Methyl cytosine
<220> FEATURE:
<221> NAME/KEY: modified_base
<222> LOCATION: (17)..(17)
<223> OTHER INFORMATION: 2'-O-Methyl adenine
<220> FEATURE:
<221> NAME/KEY: modified_base
<222> LOCATION: (18)..(18)
<223> OTHER INFORMATION: 2'-O-Methyl cytosine
<220> FEATURE:
<221> NAME/KEY: modified_base
<222> LOCATION: (19)..(19)
<223> OTHER INFORMATION: 2'-O-Methyl uracil
<220> FEATURE:
<221> NAME/KEY: modified_base
<222> LOCATION: (20)..(20)
<223> OTHER INFORMATION: 2'-O-Methyl adenine

<400> SEQUENCE: 38
cgtctctctt ccatucacua gatgag                                         26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagtagccac tcccttagga tagtg                                          25

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagtagccac tcccttag                                                  18

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aagtagccac tcccotta                                                  17

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(19)
<223> OTHER INFORMATION: Nitroindole
```

<400> SEQUENCE: 42
aagtagccac tcccttanna tagtg                                              25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (14)..(14)
<223> OTHER INFORMATION: 2'-O-Methyl cytosine
<220> FEATURE:
<221> NAME/KEY: modified_base
<222> LOCATION: (15)..(16)
<223> OTHER INFORMATION: 2'-O-Methyl uracil
<220> FEATURE:
<221> NAME/KEY: modified_base
<222> LOCATION: (17)..(17)
<223> OTHER INFORMATION: 2'-O-Methyl adenine
<220> FEATURE:
<221> NAME/KEY: modified_base
<222> LOCATION: (18)..(19)
<223> OTHER INFORMATION: 2'-O-Methyl guanine

<400> SEQUENCE: 43
aagtagccac tcccuuagga tagtg                                              25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gacatcctgg gtttaaatcc cacc                                               24

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gacatcctgg gtttaaa                                                       17

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gacatcctgg gtttaa                                                        16

<210> SEQ ID NO 47
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: Nitroindole

<400> SEQUENCE: 47
gacatcctgg gtttaanncc cacc                                           24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (13)..(14)
<223> OTHER INFORMATION: 2'-O-Methyl uracil
<220> FEATURE:
<221> NAME/KEY: modified_base
<222> LOCATION: (15)..(17)
<223> OTHER INFORMATION: 2'-O-Methyl adenine
<220> FEATURE:
<221> NAME/KEY: modified_base
<222> LOCATION: (18)..(18)
<223> OTHER INFORMATION: 2'-O-Methyl uracil

<400> SEQUENCE: 48
gacatcctgg gtuuaaaucc cacc                                           24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcgagcaaat tagtcccaat ctcc                                           24

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tcgagcaaat tagtccc                                                   17

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcgagcaaat tagtcc                                                    16
```

```
<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: Nitroindole

<400> SEQUENCE: 52
tcgagcaaat tagtccnnat ctcc                                          24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (13)..(13)
<223> OTHER INFORMATION: 2'-O-Methyl guanine
<220> FEATURE:
<221> NAME/KEY: modified_base
<222> LOCATION: (14)..(14)
<223> OTHER INFORMATION: 2'-O-Methyl uracil
<220> FEATURE:
<221> NAME/KEY: modified_base
<222> LOCATION: (15)..(17)
<223> OTHER INFORMATION: 2'-O-Methyl cytosine
<220> FEATURE:
<221> NAME/KEY: modified_base
<222> LOCATION: (18)..(18)
<223> OTHER INFORMATION: 2'-O-Methyl adenine

<400> SEQUENCE: 53
tcgagcaaat tagucccaat ctcc                                          24

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaaagagtac ccgtgccatc g                                             21

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aaaagagtac ccgt                                                     14

<210> SEQ ID NO 56
<211> LENGTH: 13
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 56
aaaagagtac ccg                                                         13

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: Nitroindole

<400> SEQUENCE: 57
aaaagagtac ccgnnccatc g                                                21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (10)..(12)
<223> OTHER INFORMATION: 2'-O-Methyl cytosine
<220> FEATURE:
<221> NAME/KEY: modified_base
<222> LOCATION: (13)..(13)
<223> OTHER INFORMATION: 2'-O-Methyl guanine
<220> FEATURE:
<221> NAME/KEY: modified_base
<222> LOCATION: (14)..(14)
<223> OTHER INFORMATION: 2'-O-Methyl uracil
<220> FEATURE:
<221> NAME/KEY: modified_base
<222> LOCATION: (15)..(15)
<223> OTHER INFORMATION: 2'-O-Methyl guanine

<400> SEQUENCE: 58
aaaagagtac ccgugccatc g                                                21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atgggtgtaa gcaggctcct                                                  20

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
```

```
atgggtgtaa gca                                                          13
```

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

```
atgggtgtaa gc                                                           12
```

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: Nitroindole

<400> SEQUENCE: 62

```
atgggtgtaa gcnngctcct                                                   20
```

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (9)..(10)
<223> OTHER INFORMATION: 2'-O-Methyl adenine
<220> FEATURE:
<221> NAME/KEY: modified_base
<222> LOCATION: (11)..(11)
<223> OTHER INFORMATION: 2'-O-Methyl guanine
<220> FEATURE:
<221> NAME/KEY: modified_base
<222> LOCATION: (12)..(12)
<223> OTHER INFORMATION: 2'-O-Methyl cytosine
<220> FEATURE:
<221> NAME/KEY: modified_base
<222> LOCATION: (13)..(13)
<223> OTHER INFORMATION: 2'-O-Methyl adenine
<220> FEATURE:
<221> NAME/KEY: modified_base
<222> LOCATION: (14)..(14)
<223> OTHER INFORMATION: 2'-O-Methyl guanine

<400> SEQUENCE: 63

```
atgggtgtaa gcaggctcct                                                   20
```

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64

```
acatccacca tccatctcct tg                                                22
```

```
<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acatccacca tccat                                                          15

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acatccacca tcca                                                           14

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: Nitroindole

<400> SEQUENCE: 67
acatccacca tccanntcct tg                                                  22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (11)..(11)
<223> OTHER INFORMATION: 2'-O-Methyl uracil
<220> FEATURE:
<221> NAME/KEY: modified_base
<222> LOCATION: (12)..(13)
<223> OTHER INFORMATION: 2'-O-Methyl cytosine
<220> FEATURE:
<221> NAME/KEY: modified_base
<222> LOCATION: (14)..(14)
<223> OTHER INFORMATION: 2'-O-Methyl adenine
<220> FEATURE:
<221> NAME/KEY: modified_base
<222> LOCATION: (15)..(15)
<223> OTHER INFORMATION: 2'-O-Methyl uracil
<220> FEATURE:
<221> NAME/KEY: modified_base
<222> LOCATION: (16)..(16)
<223> OTHER INFORMATION: 2'-O-Methyl cytosine

<400> SEQUENCE: 68
acatccacca uccauctcct tg                                                  22
```

-continued

```
<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccacaacacg tgggaattca ag                                              22

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
actgtaatga gaacaggatg ggattc                                          26

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tgtggcatgg gtcctgg                                                    17

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccagcaagca gagtgtggg                                                  19

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
ccattaagtc agccaccagt ccccc                                           25

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
tgggggactg gtggctgact taatgg                                          26

<210> SEQ ID NO 75
```

```
<211> LENGTH: 218
<212> TYPE: DNA
<213> ORGANISM: Rattus sp.

<400> SEQUENCE: 75
ggatcctcta gatgcatgct cgagtaatac gactcactat agacatggtc aaccccaccg      60
tgttcttcga catacggctg atggcgagcc cttgggtcgc gtctgcttcg agctgtttgc     120
agacaaagtt ccaaagacag cagaaaactt tcgtgctctg agcactgggg agaaaggatt     180
tggctataag atgatacact ccgacataac gtggatcc                             218

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccaaatcctt tctccccagt g                                                21

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gttttctgct gtctttggaa ctttg                                            25
```

METHODS FOR AMPLIFYING POLYMERIC NUCLEIC ACIDS

This is a continuation of application Ser. No. 10/911,652 filed on Aug. 2, 2004, which claims priority under 35 U.S.C. §119(e) to U.S. provisional patent application no. 60/492,120, filed Aug. 1, 2003, which is incorporated herein by reference in its entirety. Application Ser. No. 10/911,652 is also a continuation-in-part of application Ser. No. 10/377,168 filed on Feb. 28, 2003 and now issued as U.S. Pat. No. 7,112,406, which in turn claims priority to U.S. provisional application Ser. No. 60/360,995 filed Mar. 1, 2002.

FIELD OF THE INVENTION

The present invention relates to the field of nucleic acid replication and amplification. More specifically, the invention pertains to methods and compositions for amplifying nucleic acids using a thermostable DNA polymerase and a primer set that includes replicable and non-replicable primers.

BACKGROUND OF THE INVENTION

The polymerase chain reaction (PCR) method is commonly used to amplify specific nucleic acid polymer sequences. The procedure involves several sequential steps, including denaturation of DNA into single strands, annealing of oligonucleotide primers to a template DNA sequence, and extension of the primers with a DNA polymerase (Mullis, K. B. et al., U.S. Pat. Nos. 4,683,202, 4,683,195; Mullis, K. B., EP 201,184; Erlich, H., EP50,424, EP 84,796, EP 258,017, EP 237,362; Erlich, H., U.S. Pat. No. 4,582,788; Saiki, R. et al., U.S. Pat. No. 4,683,202; Mullis, K. B. et al. Cold Spring Harbor Symp. Quant. Biol. 51:263 (1986); Saiki, R. et al. Science 230:1350 (1985); Saiki, R. et al. Science 231:487 (1988); Loh, E. Y. et al. Science 243:217 (1988)).

In theory, the number of primer binding sites doubles with each round of PCR replication because each of the synthetic DNA strands in the reaction, including the original strands and those produced from extension reactions in previous cycles, is available to serve as a template for extending annealed primers in the next round of replication. This aspect of the method, coupled with sufficiently abundant oligonucleotide primer molecules, results in synthetic DNA accumulating in a mathematically exponential manner in successive rounds of replication. The steps in PCR can be repeated many times, to provide large quantities (amplification) of the original target sequence encompassed by the oligonucleotide primers. Even one copy of a DNA sequence can be amplified into hundreds of nanograms (ng) of product (Li, H. et al. Nature 335:414 (1988)). PCR is now a widely utilized tool in molecular biology because of its extreme power and robustness and because of the ready availability of synthetic oligonucleotide primers, thermostable DNA polymerases, and automated temperature cycling machines.

The PCR process is quite susceptible to contamination that is caused by the inadvertent transfer of DNA from one amplification reaction mixture into a subsequent reaction mixture. Even the carryover of one full-length nucleic acid polymer that spans both PCR primer binding sites can be enough to cause a false-positive result in a subsequent reaction. Because the quantities of the amplification products can be large, extreme care must be taken to avoid this problem (Kwok, S. and Higuchi, R. Nature 339:237 (1989)). The presently known procedures for avoiding carryover contamination increase the technical difficulty of carrying out a PCR assay and add significantly to an assay's cost.

One technique for reducing the risk of carry-over contamination has been developed. The technique, known as linked linear amplification (also referred to as "LLA"), uses amplification primers that are modified in such a way that they are, or are rendered, replication defective, non-replicable, or blocked. Primers that have an internal blocking group, such as 1,3-propanediol, can support primer extension and can give rise to amplicons but in subsequent rounds of replication those amplicons give rise to amplicons that terminate in the vicinity of the blocking group and therefore contain only a portion of the primer binding site which is not sufficient for primer binding. See, for example, U.S. Pat. Nos. 6,335,184 and 6,027,923. See, also, Reyes et al. Clinical Chemistry 47:1 31-40 (2001); Wu et al. Genomics 4: 560-569 (1989).

Because the amplicons generated from primer extension products in LLA cannot serve as templates for subsequent primer binding and therefore extension, this DNA does not interfere with subsequent LLA amplification reactions. Although in theory LLA may avoid the cross contamination problem, it requires an extraordinary number of reaction cycles and/or primers to achieve suitable levels of amplified products. For example, U.S. Pat. No. 6,335,184 discloses that 1,000 cycles would be necessary in order to generate a yield of 500,500 products, as opposed to 30 cycles with PCR. The number of reaction cycles can be reduced to some extent by including numerous LLA primers in the amplification reactions. However, Reyes et al. suggest that 14 to 18 primers would be needed to achieve amplification yields comparable with PCR. Clinical Chemistry 47:31-40 (2001). Clearly, this is not a practical solution to the carryover contamination problem because designing and synthesizing such a large number of primers is time consuming and expensive and in most cases it simply isn't possible because there are not a sufficient number of primer-binding sites available and the use of such a large number of primers can poison amplification reactions.

Several other approaches have been developed to avoid the long recognized problem of PCR product contamination. These approaches include chemical decontamination, utilizing closed systems, use of ultra-violet irradiated work stations (Pao et al., Mol. Cell. Probes 7: 217-9 (1993)), cleavable primers (Walder et al., Nucleic Acids Research 21:4, 229-43 (1993))), or enzymatic degradation methods (Longo et al., Gene 93: 125-8 (1990)). None of these methods is totally effective and they involve additional processing steps that complicate the amplification method.

Thus, a need exists for new compositions and methods for routinely amplifying nucleic acids such that the problems associated with carryover-contamination are minimized and which provide suitable levels of amplification without using an excessive number of amplification primers. Ideally such compositions could be used in methods that would provide single-stranded nucleic acid products for direct use in diagnostic methods.

Examples of such compositions and methods have been set forth in U.S. patent application Ser. No. 10/377,168 ("Polynomial Amplification of Nucleic Acids", filed Feb. 28, 2003) and in International application no. PCT/US2003/006293 (WO03074724; published Sep. 12, 2003), each of which is herein incorporated herein by reference in their entirety. Although the compositions and methods set forth in these applications solve many of the problems set forth above associated with the amplification of nucleic acids, further research has led to improvements, set forth herein, in these compositions and methods for the amplification of nucleotide sequences from a nucleic acid polymer in a high complexity nucleic acid sample, such as genomic DNA.

SUMMARY OF THE INVENTION

The invention provides compositions and methods for amplifying nucleic acid polymer sequences. The unique compositions of the invention include a primer set composed of a mixture of two types of primers for DNA synthesis. For extension in one direction, the primers all contain modifications that destroy their ability to serve as templates that can be copied by DNA polymerases. For extension in the opposite direction, the set includes at least one primer that can serve as a template and be replicated by DNA polymerases throughout its length. The method can be carried out by mixing the nucleic acid polymer sequence of interest with the set of DNA synthesis primers in an amplification reaction mixture. The reaction mixture is then subjected to temperature cycling analogous to the temperature cycling in PCR reactions. At least one primer in the primer set hybridizes to the nucleic acid polymer. It is preferred that the non-replicable primer hybridizes to the nucleic acid polymer and is extended to produce an extension product that contains sequence from the nucleic acid polymer to which the replicable primer then hybridizes. Of course, if the nucleic acid polymer is double stranded, both the replicable and nonreplicable primers will hybridize and be extended by DNA polymerase.

One advantage of the method is that it efficiently generates extension products that cannot be efficiently amplified in subsequent reactions with the same primer set. Another advantage of the method is that it generates substantial quantities of single-stranded DNA. The single-stranded DNA is the extension product of the replicable primer. The method is ideally suited to the amplification of DNA found in genomic and other highly complex DNA samples.

The present invention provides for methods for amplifying a nucleotide sequence from a nucleic acid polymer in a high complexity nucleic acid sample, comprising: contacting a nucleic acid polymer in a high complexity nucleic acid sample with a primer set comprising (i) a non-replicable primer that hybridizes to the nucleic acid polymer, wherein the non-replicable primer comprises at least four adjacent 2'-O-alkyl riboses and (ii) a replicable primer that hybridizes to a primer extension product generated by replication of the nucleic acid polymer from the non-replicable primer, under conditions such that a primer extension product that is capable of hybridizing to the replicable primer is produced using the nucleic acid polymer as a template and the non-replicable primer as the primer, wherein the primer extension product contains a portion of the nucleotide sequence of the nucleic acid polymer or its complement.

The present invention also provides for kits for amplifying a nucleic acid polymer in a high complexity nucleic acid sample comprising a primer set, which primer set comprises (i) a non-replicable primer that hybridizes to a polymeric nucleic acid, wherein the non-replicable primer comprises at least four adjacent 2'-O-alkyl riboses and (ii) a replicable primer that hybridizes to a primer extension product generated by replication of the nucleic acid from the non-replicable primer.

In a preferred embodiment, the primer extension product is separated from its nucleic acid polymer template and the resulting mixture is treated with the primer set under conditions such that primer extension products are produced. In a further embodiment, the step of separating the primer extension product from its nucleic acid polymer template is repeated from about 20 to about 60 times and the resulting mixture is treated with the primer set under conditions such that primer extension products are produced. The extension products from the non-replicable primers of the methods and kits of the present invention have a sterilization number of about 10 or more, or preferably of about 100 or more, or more preferably of about 1000 or more, and even more preferably of about 10,000 or more.

The nucleic acid polymer used in the methods and kits of the invention can comprise a double-stranded region such that primer extension products are produced by both the non-replicable primer and the replicable primer. In addition, or alternatively, the methods and kits of the present invention can be used, for example, to amplify a nucleotide sequence from a nucleic acid polymer that comprises a single-stranded region. In a preferred embodiment, the high complexity nucleic acid sample of the methods and kits of the invention is genomic DNA.

The primer set used in the methods of the invention and provided in the kits of the invention can further have a second, a third, or preferably one to five non-replicable primers which hybridize to the polymeric nucleic acid.

The methods and kits of the present invention produce about $10^2$ or more copies of product, or preferably about $10^4$ or more copies of product, or more preferably about $10^5$ or more copies of product, or even more preferably about $10^6$ or more copies of product, or most preferably about $10^7$ or more copies of product.

In one embodiment of the invention the non-replicable primer has at least six 2'-O-alkyl riboses. In a preferred embodiment of the invention the 2'-O-alkyl riboses of the non-replicable primer are 2'-O-methyl riboses, and in a particularly advantageous embodiment of the invention the non-replicable primer comprises at least six adjacent 2'-O-methyl riboses. In a further embodiment of the invention, the replicable primer is labeled for detection.

In a further embodiment of the invention, each primer is present in a concentration from about 0.6 µM to about 5 µM, and, preferably, at a concentration is about 2 µM. In yet another embodiment of the invention, magnesium is present in the amplification reaction in a concentration of about 3 mM to about 6 mM, or preferably, at a concentration of about 5 mM.

DETAILED DESCRIPTION OF THE INVENTION

The present invention provides a novel method for amplifying polymeric nucleotide sequences in a high complexity nucleic acid sample. The method can be carried out by mixing the nucleic acid polymer of interest with a unique set of DNA synthesis primers in an amplification reaction mixture. The amplification reaction mixture is then subjected to temperature cycling, analogous to the temperature cycling in PCR reactions. The method is unique in that all of the DNA synthesis primers that are extended in one direction contain modifications that prevent them from serving as templates for replication. Consequently, when amplicons produced from these primers are replicated in a subsequent extension reaction the products do not contain binding sites for the primer that initiate the original strand. These primers are termed non-replicable primers for purposes of this invention. The DNA synthesis primer(s) in the opposing direction are replicable as is any PCR primer. By using such a combination of replicable and non-replicable primers, the amplification method produces more amplicons than in LLA. In fact, using the described methods polynomial amplification yields can approach the yields obtained from PCR.

The amplification method is carried out with a unique primer set. As indicated above, the primer set includes two types of DNA synthesis primers. One type of primer is replicable and the other is non-replicable. Replicable primers include oligonucleotides that hybridize to a nucleic acid polymer in a reaction mixture, prime the extension of a nucleic acid polymer strand by a DNA polymerase in an extension reaction, and serve as templates, throughout their entire length, for extension of complementary strands. Replicable primers include oligonucleotides that have no chemical modifications, and include PCR primers, as are well known in the art.

Non-replicable primers include oligonucleotides that can hybridize to a nucleic acid polymer in a reaction mixture, prime the extension of a nucleic acid polymer strand by a DNA polymerase in an extension reaction, but cannot serve as templates throughout their entire length. More specifically, non-replicable primers include oligonucleotide primers that have modified structures such that a polymerase catalyzing an extension reaction and using the non-replicable primer as a template cannot copy it. Consequently, a non-replicable primer will tend to prevent a polymerase from generating a strand containing a new binding site for the same non-replicable primer when a strand containing a nonreplicable primer is itself used as a template.

Preferably, when a non-replicable primer serves as a template for DNA synthesis the growing nucleic acid polymer will terminate at a precisely defined location in close proximity to the site of the modification and the 3'-termini of the population of amplicons will have the same 3'-terminal nucleotide. In some cases additional residues can be added after the modification and this does not interfere with the utility of the method so long as the original non-replicable primer-binding site is not regenerated. Moreover, the utility of the method is not appreciably affected when amplicons having a mix of termination points are synthesized as long as the largest component of amplicons terminates at a uniform location.

Any number of non-replicable primers can be included in a primer set as long as the non-replicable primers provides for sufficient amplification. For example, in some methods between 1 and 10 non-replicable primers can be included in the primer set. To improve yields in the method two or more non-replicable primers are preferred. More preferred is a primer set that includes at least three non-replicable primers and still more preferred four non-replicable primers. Substantial amplification in the polynomial amplification reaction has been observed with four and five non-replicable primers. For example, all non-replicable primers in a primer set bind to the same template strand and are extended in the same direction. At least one replicable primer is also included in the primer set. This replicable primer binds to the opposite strand as the non-replicable primers.

The term "nested," when used to describe primers, has its ordinary meaning in the art of nucleic acid hybridization. Specifically, "nested primers" are capable of hybridizing to positions on the nucleic acid adjacent to the nucleotide sequence of interest that are bracketed by the most distal primer pair positions (i.e., the non-replicable primer and position of hybridization of the replicable primer on the complementary nucleic acid strand that are farthest apart).

Numerous oligonucleotide modifications are known and can be used for generating non-replicable primers. Suitable modifications can be identified by one of skill in the art by incorporating one or more modifications into a primer, carrying out an amplification reaction, and evaluating amplicon yields, as in Example 4 below, for example. In these experiments useful modifications will give lower yields of amplicons than would be the case when an unmodified primer that binds to the same primer-binding site. Alternatively, modifications can be incorporated directly into a synthetic template and a primer used in a primer extension reaction to determine whether extension past the modified residue(s) occurs to any appreciable extent. This approach can be carried out in a cycling reaction format.

Using these approaches several suitable modifications have been identified. Suitable modifications include modifications of the base moiety, the carbohydrate moiety, and the phosphate. These modifications are not mutually exclusive. For example, 1,3-propandiol lacks both the carbohydrate and base moiety.

Suitable modifications to the base moiety include the complete absence of a base (abasic residues), incorporation of modified bases such as iso-cytidine, iso-guanidine, and the direct modification of otherwise normal base moieties with groups such as nitroindole.

Suitable modifications to the sugar moiety include the alkylation of the 2'-hyroxyl group, substitution with a 3 carbon spacer group, and substitution of the 2'-deoxyribose with 1,4-anhydro-2-deoxy-D-ribitol (d-spacer CE phosphoramidite; Glen Research, Sterling, Va.), incorporation of 2'-deoxyribofuranosyl naphthalene groups. Suitable three carbon spacers include propane, propanol, and 1,3-propanediol. Of these, 1,3-propanediol is preferred and is known as the C3 spacer for purposes of this specification, unless otherwise indicated.

Suitable phosphate modifications include phosphoramidates, phosphotriesters, methyl phosphonates, for example.

Although any of these or other modifications can be used in the invention, it has been discovered that alkylation of the 2-hydroxy group of ribose yields better results. Alkylation can be with any suitable alkyl group including $C_1$-$C_6$ straight- or branched-chain alkyl groups. Although any alkylation can be used, it has further been discovered that 2'-O-methyl groups are preferred.

Each of the oligonucleotide modifications mentioned above can be incorporated into oligonucleotides during their chemical synthesis using suitable phosphoramidite precursors by methods known in the art. For example, primers that contain a residue of 1,3-propanediol can be synthesized according to the method described in Seela et al., *Nuc. Acids Res.* 15, 3113-3129 (1987) from commercially available starting materials, e.g., from Glen Research (Sterling, Va.) and Pierce (Milwaukee, Wis.). Primers containing a residue of 1,4-anhydro-2-deoxy-D-ribitol, the model for the abasic site, can be synthesized according to methods described in Eritja et al., *Nucleosides & Nucleotides* 6, 803-814 (1987).

Published European Patent Application No. 416,817 A2 describes the synthesis of primers containing one or more 2' deoxyribofuranosyl naphthalene moieties as non-replicable elements between a primer sequence and a polynucleotide tail. The synthesis of oligonucleotide primers that contain other elements that halt polymerase-dependent copying of the template, such as derivatives of ribonucleosides and deoxyribonucleosides, will be apparent to those who are skilled in the art.

Another type of non-replicable primer incorporates cleavable elements that provide for cleavage after a primer is incorporated into a prima extension product and before that extension product is completely copied when used as a template. Suitable cleavable elements are cleavable under conditions that do not damage the remainder of the extension product or the template to which it anneals. Such a cleavage event will lead to a truncated amplicon that does not contain the original primer binding site. One exemplary cleavable element is one or more ribonucleotides incorporated into primers, preferably at their 3'-termini. When such a primer is annealed to a target DNA and an extension reaction initiated a ribonuclease that recognizes the ribonucleotide can cleave at the site of the ribonucleotide thereby removing the portion of the amplicon that is toward the 5'-end of the amplicon.

Any number of modifications can be included in an oligonucleotide primer so long as the primer can selectively hybridize to its intended location and the number is sufficient to block extension reactions. Two, three, four, five, and six modifications or more may be present so long as extension is blocked and the oligonucleotides can prime extension reactions. Where multiple modifications are present in an oligonucleotide they may be the same or different. The modifications can be at any location in the oligonucleotide so long as they are sufficient to prevent the regeneration of a primer-binding site when the complement strand is synthesized. Where the modification is 2'-O-methyl-ribose, which is preferred, it is preferred that at least four, and preferably six or at least six, adjacent modifications reside in the oligonucleotide primer.

Specific examples of modifications that block extension reactions without allowing any appreciable of extension through them include two adjacent C3 spacers, two adjacent d-spacers, two adjacent nitroindole modified oligonucleotides, and six adjacent 2'-O-methyl modifications. Oligonucleotides containing single C3 spacer, d-spacer, and nitroindole modifications did not block extension reactions sufficiently.

Although any nucleic acid polymer to which the primers of the invention can bind can serve as a template for a DNA polymerase for amplification by the methods described herein, it has been discovered that the advantages of the described methods and compositions are best realized when utilized on nucleic acid polymers in a high complexity nucleic acid sample. A high complexity nucleic acid sample is one in which there is a high number of different nucleic acid polymers in the sample. Examples of high complexity nucleic acid samples include genomic DNA and a cDNA library made from a high complexity RNA sample. Other suitable nucleic acid polymers include amplified polymeric sequences containing copies of such sequences; cloned DNA, such as plasmid DNA; segments of cloned DNA; and DNA obtained from reverse transcription of RNA. Suitable nucleic acid polymers include single and double stranded polymers.

The present method is particularly well suited to the amplification of sequences from complex mixtures, such as from genomic DNA preparations. However, as previously indicated, any mixture in which nucleic acid polymer sequences are found can be used in the present method so long as the mixture does not interfere significantly with DNA polymerase enzyme activity and amplification.

To optimize amplification, it can be necessary in some situations to modify the nucleic acid polymer mixtures. For example, when the nucleic acid polymer mixture contains solutes that interfere with the amplification reaction, it may be necessary to remove or substitute for these solutes through desalting or ion exchange procedures. It may also be necessary to add protease inhibitors, chelators, and buffers, to the polymer mixture or to the amplification reaction to optimize the reactions. It is well within the skill of one of skill in the art to recognize the need for such modifications as well as to carry out appropriate modifications.

The method involves contacting the desired nucleic acid polymer with a primer set. Any method of contacting the two components that allows the primers to anneal to the nucleic acid polymer and allows the nucleic acid polymer to serve as a template for the extension of one or more of the primers is suitable. This step can be conveniently accomplished by adding a solution containing one of the components to a solution containing the other. Alternatively, a solution containing one of the components could be added to the other component in dried form and the dried component dissolved into the solution, or the components can be dried together and redissolved in a third solution.

The primer sets of the invention can hybridize to the nucleic acid polymer where they contain sufficiently complementary sites. A primer is said to hybridize to another nucleic acid polymer molecule, such as a cDNA, genomic DNA, or RNA, when it anneals to the nucleic acid polymer molecule under the appropriate conditions of temperature and solution ionic strength. Hybridization requires that two nucleic acids (e.g., a primer and nucleic acid polymer) that contain sufficiently complementary sequences such that under the appropriate conditions (stringency) the nucleic acids bind to each other. The conditions of temperature, ionic strength, and pH determine the "stringency" of the hybridization. The appropriate stringency for hybridizing nucleic acids depends on the length of the nucleic acids and the degree of complementation, variables well known in the art. The greater the degree of similarity or homology between two nucleotide sequences, the greater the stability for hybrids of nucleic acids having those sequences. One measure of stability is the melting temperature (Tm) of the oligonucleotide. The melting temperature is generally regarded as the temperature at which a duplex nucleic acid dissociates into single-stranded nucleic acids. Shorter primers generally anneal to their binding sites only at lower melting temperatures. For purposes of this invention a primer need not contain a completely complementary sequence for its binding site but must be sufficiently complementary for hybridization or annealing to occur.

Primers, once hybridized to a nucleic acid polymer may function in polynomial amplification methods of the invention as substrates for polymerization catalysts. The 3'-end of the primer can be elongated, in the presence of adequate nucleotides and a polymerase, such that a strand is generated that is complementary to the template nucleic acid polymer sequence. Thus, a non-replicable primer can hybridize to a nucleic acid polymer and can be elongated to generate a primer extension product that is complementary to the template. Likewise, a replicable primer can hybridize to a nucleic acid polymer and can be elongated to generate a primer extension product that is complementary to its template. Similarly, the replicable primer in a primer set will be capable of hybridizing to the primer extension product generated by replication of the nucleic acid polymer from the non-replicable primer. The hybridizing and extension process can be repeated by denaturing the resulting duplex nucleic acid with heat, permitting the primers to anneal to the nucleic acid polymer strands and again carrying out the primer extension reaction.

Suitable conditions for producing primer extension products from hybridized primers of this invention can be used in polynomial amplification. Such conditions are well known in the art and include the presence of the four common nucleoside triphosphates, a polymerization catalyst, an appropriate buffer, appropriate salts in solution with the primer set and nucleic acid polymer and suitable temperatures.

All four nucleoside triphosphates are generally included in the polynomial amplification reaction mixtures. Any suitable concentration that provides for efficient amplification can be used. For example, suitable concentrations of each nucleotide triphosphate in the reaction mix can range from about 10 µM to about 400 µM. Preferably, the nucleotide concentration for each nucleotide will range from about 100 µM to about 300 µM. The most preferred nucleotide triphosphate concentration is about 200 µM.

Any suitable primer concentration that provides for efficient amplification can be used. Although primer concentrations from about 0.2 µM to about 10 µM can be used with the present methods, it has been discovered that a primer concentration range from about 0.6 µM to about 5 µM yields better results and, still a concentration of about 2 or about 3 µM is even more preferable.

The polymerization catalyst in the polynomial amplification reaction mixtures can be any catalyst that is capable of extending a 3'-hyroxyl group of an oligonucleotide primer annealed to a nucleic acid polymer using the nucleic acid as a template. Suitable catalysts add nucleotides such that they can form hydrogen bonds with the bases of the nucleic acid polymer. Catalysts include enzymes and more specifically polymerases that are capable of replicating nucleic acid polymers in vitro. Suitable polymerases include E. coli DNA polymerase I, TAQ polymerase, Klenow fragment of E. coli DNA polymerase I, T4 DNA polymerase, reverse transcriptase (where the template is RNA and the extension product is DNA), or a thermostabile DNA polymerase. DNA polymerases that are thermostable and have 5'-3' exonuclease activity are preferred. Commercially available polymerases such as Amplitaq Gold® DNA polymerase and Imolase™ are preferred. Any suitable concentration of polymerase that can provide the needed quantities of amplified nucleic acid polymers can be used. For example, the concentration of Ampli-Taq Gold or Imolase™ used can range from about 0.1 to about 5 units per 50 µl reaction and 2.5 units is most preferred.

Buffers that are thermostable and have a pK within about 1 pH unit from the optimal pH of the catalyst at the temperature of the extension reaction can be used in the polynomial amplification reaction mixtures. Thermostable buffers are chemically stable when exposed to varying temperatures in the range of about 0° C. to about 100° C. during the course of temperature cycling. For example, with certain thermostable polymerases the optimum pH is about 7 to about 8 and suitable buffers in reactions with these polymerases will have pKs in the range of about 6 to about 9 at the temperature of the extension reaction. Preferably, Tris (tris hydroxymethyl amino methane) buffer is used with a chloride counter ion at a pH of about 8.3. When Tris.Cl is included in reaction mixtures the preferred concentration is about 10 mM, although concentrations of from about 5 mM to 100 mM can be used.

Any appropriate salt concentration can be included in polynomial amplification reaction mixtures to optimize the yield of amplicons. Preferred salts include monovalent and divalent ion species. Particularly preferred salts include KCl and $MgCl_2$ and more preferred is a mixture of these two salts. Any concentration of these species that provides for efficient polynomial amplification can be used. For example, from about 5 mM to about 150 mM KCl can be included in the polynomial amplification reactions. More preferably, from about 10 mM to about 100 mM KCl is used, still more preferably from about 25 mM to about 75 mM KCl is used, and most preferably about 50 mM KCl is included in reaction mixtures. With respect to $MgCl_2$, from about 1 mM to about 10 mM $MgCl_2$ can be used in polynomial amplification reactions. More preferably, from about 2 mM to 8 mM $MgCl_2$ is used. Although amplification reactions can be done using a range of magnesium concentration from about 2 mM to about 8 mM magnesium, it has been discovered that from about 3 mM to about 6 mM magnesium yields better results, and that 5 mM magnesium is particularly preferred.

The amplification conditions also include a suitable temperature regimen. Depending on the primer length and sequence, annealing temperatures of about 35° C. to about 75° C. can be used, and a temperature of about 55° C. to about 75° C. can be used for the primer extension reaction. The preferred temperatures for annealing and extension will depend on the nature of the primer and can require optimization. The duration of each temperature step in the temperature cycling can range from a few seconds to minutes. It is well within the skill of one having skill in the art to optimize these temperatures and their duration in the temperature cycling method.

The optimal reaction conditions for polynomial amplification may vary slightly from those typically used in amplification reactions that do not use non-replicable primers. The modifications that give rise to non-replicable elements can require that the primer annealing temperature be raised or lowered as compared to a primers unmodified counterpart. For example, when the base analog 1,3-propanediol is included in an oligonucleotide primer, an annealing temperature that is about 5° C. lower than for the unmodified oligonucleotide primer can be advantageous.

After treating the reaction mixture with sequential temperature steps that include treatment with an annealing temperature and an extension temperature the primer extension product can be separated from its nucleic acid polymer template by heating the reaction mixture sufficiently. Heating the polynomial amplification reaction to a temperature of over about 90° C. and more preferably to about 95° C. can displace annealed strands. The resulting mixture can then be treated again with the excess primers that reside within the reaction mixture by incubating the reaction mixture again at the annealing temperature and then the extension temperature so that an additional round of annealing and extension occur to produce additional primer extension products. The temperature cycling can be repeated for as many times as is necessary to generate the required amount of amplification product. For example, the temperature cycling can be repeated from about 20 to about 60 times.

When cycling is complete the product amplicons from the polynomial amplification reaction can be characterized as having a certain amount of sterility. The term "sterile" for purposes of this application indicates that the products do not serve as templates for further amplification reactions with the same primers (and for other primers that bind outside of these primers), and therefore will not act as a contaminant in subsequent reactions. The predominant species of molecule produced in a polynomial amplification reaction of the invention will be nucleic acid polymers that are incapable of hybridization with any primers used in the polynomial amplification system. For example, depending on the number of cycles of replication, operation of the invention in its simplest form will result in a product in which 80% or more of the primer extension products will be fully incapable of serving as a template for further replication. After additional replication cycles, the relative amount of contaminating nucleic acids is reduced further, to the point where their levels become insignificant or even undetectable. The sterilization number is a quantitative measure of the reduced amount of product produced in a polynomial amplification reaction when polynomial amplification products are used as the target as compared to when the same number of targets in a high complexity nucleic acid sample is amplified. Thus, for example, when a genomic DNA mixture containing $10^4$ targets is amplified by a certain amount under certain conditions and a sample of $10^4$ targets from a polynomial amplification reaction is used a target and produces 10-fold less amplification product under the same conditions, the sterilization number for the product from the polynomial amplification reaction mixture is 10. In making this determination the primers used in the first polynomial amplification reaction are also used with the genomic DNA target and the targets from the polynomial amplification reaction mixture.

Utilizing the disclosed polynomial amplification methods, products having a sterilization number of about 10 or more can be produced. Products having a sterilization number of about 100 or more can also be produced. Preferably products having sterilization numbers of about 1,000, even more preferably about 10,000 or more are produced by the disclosed methods. It can be appreciated that the sterility number will increase as the number of cycles and the number of nonreplicable primers increase such that sterility numbers of even 100,000 can be obtained.

These sterility numbers have been achieved while at the same time efficiently producing amplicons. For example, the above sterility numbers can be obtained while at the same time obtaining about a $10^2$-fold amplification. More preferably the sterility numbers are obtained with about a $10^3$-fold amplification, more preferably $10^4$, even more preferably about $10^5$, or even more preferably a $10^6$-fold amplification. Yet more preferable is $10^7$-fold or more amplification of a product that has sterility as discussed previously.

In some cases, it may be desirable to first make multiple copies of a target sequence using a linear amplification reaction. In a linear amplification reaction, a single primer is used and only one strand is copied. The product can be isolated on a solid support using an affinity group attached to the primer, such as biotin, or by hybridization to an immobilized nucleic acid fragment complementary to a portion of the desired extension product. Cell debris and other impurities as well as the background DNA are then washed away. After release of the target sequence from the support, polynomial amplification can be performed. Such a procedure can be done, for example, when it is desired that only the strand being amplified, and not its complement, will be present during the polynomial amplification reaction.

In certain embodiments and methods primers, preferably replicable primers, can be modified with a label capable of providing a detectable signal, either directly or indirectly. Exemplary labels include radioisotopes, fluorescent molecules, biotin, and the like. Many suitable fluorophores are known and can be used, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, Nonisotopic DNA Probe Techniques, 1992, Academic Press San Diego, Calif.). It is within the skill of one of skill in the art of molecular biology to incorporate such labels into primers.

In certain methods it is preferred to first make multiple copies of the target sequence by performing multiple cycles, preferably 10-20 cycles, of PCR and then carry out the polynomial amplification reaction. This method may be particularly preferable in instances when a very low copy number of a sequence to be amplified is present in a sample.

In one embodiment of the invention, the reagents necessary to carry out polynomial amplification in diagnostics, forensics, and genotyping, can be provided in a kit. The invention provides such reagent kits for use in amplifying a particular nucleic acid sequence. Such a kit will typically contain a DNA polymerase and a primer set as described previously. Optionally, the kit may also contain a control nucleic acid sequence capable of being replicated by the primers and DNA polymerase. The replicable primer may be labeled or may contain the reagents necessary to accomplish labeling. The kit also may contain a nucleic acid probe capable of indicating the presence or absence of an amplification product of the particular sequence. The kit may also contain instructions to indicate, for example, what concentration of primers and magnesium to use in the amplification reaction. Where the kit contains primers incorporating a cleavable element, it may also contain reagents for cleaving the primer at the cleavable element.

The following examples further illustrate the invention but, of course, should not be construed as in any way limiting its scope.

EXAMPLE 1

This and the following examples demonstrate the use of the polynomial amplification system for amplification of a human genetic locus, the NOD2 gene (SEQ ID NO: 48), from human genomic DNA.

Amplification primers were chosen to have similar melting temperatures, minimal secondary structure, minimal propensity to form heterodimers, and minimal risk of cross-hybridization as determined by a GenBank Blast search. The sequence of the genetic locus and primer binding sites is shown below in Table 1. The emboldened sequence represents the primer binding sites and the corresponding arrows represent the direction in which the primers are extended. Thus, the "For" primers extend to the right in the sequence. The primers designated "Rev" extend to the left and have sequences that are complementary to the sequence shown.

TABLE 1

Oligonucleotide Primer Binding Sites For the NOD2 Locus

For-0000
cccaatgagctcatcaacaaaggctcagtaccatcagtgaaatgtaaccgtc
             >>>>>>>>>>>>>>>>>>>>>>>>>>>      >>>>

For-000                                  For-00
tctcttccattcactagatgagtttatcaaattaagtagccactcccttaggatagtggt
>>>>>>>>>>>>>>>>>>>>>         >>>>>>>>>>>>>>>>>>>>>>>

For-0
taagtacctgcattttagtgctagacatcctgggtttaaatcccacctacaccacttctt
                        >>>>>>>>>>>>>>>>>>>>>>>>

For-1
ttttgatctcgagcaaattagtcccaatctcctcattggtaaaatgggcctaaaagagta
        >>>>>>>>>>>>>>>>>>>>>>>>                     >>>>>>>>>

For-2                                         For-3
cccgtgccatcgagcataagaatctaaattgtgatgggtgtaagcaggctcctattcaca
>>>>>>>>>>>                    >>>>>>>>>>>>>>>>>>>    >>>

TABLE 1-continued

Oligonucleotide Primer Binding Sites For the NOD2 Locus

```
         For-4                  PCR-For            NOD2-probe
tccaccatccatctcct[tgtggcatgggtcctgggccattaagtcagccaccagtccccc
>>>>>>>>>>>>>>>>>
                   >>>>>>>>>>>>>>>>>      ------------------------

PCR-Rev
attacctccccacactctgcttgctgg]gaagacccaccactctctgcatgcctaaaacac
<<<<<<<<<<<<<<<<<<

Rev-1
ttgcacagtacttgatatggtttggctgtgtccccacccaaatctcttgaattcccacgt
                                              <<<<<<<<<<<<<<<

Rev-2
gttgtgggagcgacccagtggaaggtaattgaatcccatcctgttctcattacagtaaat
<<<<<<                         <<<<<<<<<<<<<<<<<<<<<<<<
```

The composition of the reaction mixtures for polynomial amplification in Example 1 is as shown below in Table 2:

TABLE 2

| Polyamp Reaction Mixture Ingredients |
| --- |
| 10 mM Tris pH 8.3 |
| 50 mM KCl |
| 5.0 mM MgCl$_2$ |
| 400 µM dNTPs (100 µM each) |
| 10 ng human genomic DNA |
| 200 nM (10 pmoles) each forward (modified) primer oligonucleotide |
| 200 nM (10 pmoles) reverse primer oligonucleotide |
| 2.5 units Amplitaq Gold ® DNA polymerase µl final volume |

The order of addition of the Table 2 components was not critical; however the enzyme was usually added last. The temperature cycle for the polynomial amplification reactions began with heating at 95° C. for 15 min followed by 30, 40, or 50 cycles of a 3-step cycle with 95° C. for 30 sec, 55° C. for 60 sec, and 72° C. for 30 sec, and then reactions were incubated at 72° C. for 3 min. Reactions were diluted to 100 µl volume with water after cycling.

Following the polynomial amplification reaction a real-time quantitative PCR assay was carried out on the products of an amplification reaction to quantitate the products from the polynomial amplification reaction. The polynomial amplification reaction product mixtures were diluted to 100 µL prior to addition to PCR assay and 1 µL was added to the PCR reactions. The real-time quantitative PCR assay utilized the oligonucleotides shown below in Table 3, which were internal to the primers used in the polynomial amplification reactions shown above in Table 1.

TABLE 3

| | Sequence | Tm | SEQ ID NO |
| --- | --- | --- | --- |
| For | TGTGGCATGGGTCCTGG | 57.9 | 49 |
| Rev | CCAGCAAGCAGAGTGTGGG | 59.3 | 50 |
| S Probe | Fam-CCATTAAGTCAGCCACCAGTCCCCC-BH1 | 64.8 | 51 |
| AS Probe | Fam-TGGGGGACTGGTGGCTGACTTAATGG-BH2 | 64.8 | 52 |

The quantitation standard for the PCR assay was the entire NOD2 locus that was cloned in the TOPO TA cloning vector pCR2.1-TOPO from Invitrogen (Carlsbad, Calif.) from a PCR fragment generated with the primers, SEQ ID NO: 49 and SEQ ID NO: 90. The components in the PCR reaction mixture are shown below in Table 4.

TABLE 4

| PCR Reaction Mixture |
| --- |
| 20 mM Tris pH 8.4 |
| 50 mM KCl |
| 3.0 mM MgCl$_2$ |
| 200 µM each dATP, dGTP, and dCTP |
| 400 µM dUTP |
| 0.5 units Uracil-DNA-N-deglycosylase |
| 1.0 unit Taq DNA polymerase |
| 50 nM Reference Dye |
| 200 nM Primer For-3 |
| 200 nM Primer Rev-3 |
| 200 nM Probe |
| 1 µl Polynomial amplification reaction product mixture |
| 25 µl final volume |

Temperature cycles employed in PCR were as follows: 50° C. (or 55° C.) for 2 min and 95° C. for 10 min followed by 40 cycles of 95° C. for 15 sec and 60° C. for 1 min. Control reactions were run with known amounts of the plasmid DNA containing the NOD2 genomic subclone to establish a standard curve with data points at $1\times10^2$, $1\times10^4$, $1\times10^6$, and $1\times10^8$ targets. All data points were performed in triplicate.

As a positive control for the polynomial amplification reactions, PCR reactions were routinely carried out with primers that bind the same binding sites in the NOD2 locus as the polynomial amplification primers using the same primers and reaction mixtures as in the polynomial amplification reaction but lacking chemical modifications.

Following an amplification reaction the amplification products were electrophoretically separated in an 8% acrylamide gel containing 1×TBE and 7M urea. Gels were treated with GELSTAR® stain and viewed according to the manufacturer's instructions. The intensity of the DNA bands observed in gels after PCR was used to determine the amount of product produced in the polynomial amplification reactions by reference to the standard curve.

The primers used in this and the following examples are listed below in Table 5. The modifications are as follows: x designates the C3 carbon spacer that is substituted for a nucleotide at the position of the oligonucleotide; nitroindole modification of the base moieties is designated with an "y"; a methoxy group bound to the 2-position of the ribose ring is designated with bold small case letters corresponding to the normal base designations, i.e., a, c, g, and u.

TABLE 5

| Binding Site | Test Oligonucleotide Primers | SEQ ID NO |
|---|---|---|
| For-0000 | CAACAAAGGCTCAGTACCATCAGTG | 49 |
| For-0000 | CAACAAAGGCTCAGTACCxTCAGTG | 50 |
| For-0000 | CAACAAAGGCTCAGTACxxTCAGTG | 51 |
| For-0000 | CAACAAAGGCTCAGTACyyTCAGTG | 52 |
| For-0000 | CAACAAAGGCTCAguaccaTCAGTG | 53 |
| For-000 | CGTCTCTCTTCCATTCACTAGATGAG | 54 |
| For-000 | CGTCTCTCTTCCATTCACTxGATGAG | 55 |
| For-000 | CGTCTCTCTTCCATTCACxxGATGAG | 56 |
| For-000 | CGTCTCTCTTCCATTCACyyGATGAG | 57 |
| For-000 | CGTCTCTCTTCCATucacuaGATGAG | 58 |
| For-00 | AAGTAGCCACTCCCTTAGGATAGTG | 59 |
| For-00 | AAGTAGCCACTCCCTTAGxATAGTG | 60 |
| For-00 | AAGTAGCCACTCCCTTAxxATAGTG | 61 |
| For-00 | AAGTAGCCACTCCCTTAyyATAGTG | 62 |
| For-00 | AAGTAGCCACTCCcuuaggATAGTG | 63 |
| For-0 | GACATCCTGGGTTTAAATCCCACC | 64 |
| For-0 | GACATCCTGGGTTTAAAxCCCACC | 65 |
| For-0 | GACATCCTGGGTTTAAxxCCCACC | 66 |
| For-0 | GACATCCTGGGTTTAAyyCCCACC | 67 |
| For-0 | GACATCCTGGGTuuaaauCCCACC | 68 |
| For-1 | TCGAGCAAATTAGTCCCAATCTCC | 69 |
| For-1 | TCGAGCAAATTAGTCCCxATCTCC | 70 |
| For-1 | TCGAGCAAATTAGTCCxxATCTCC | 71 |
| For-1 | TCGAGCAAATTAGTCCyyATCTCC | 72 |
| For-1 | TCGAGCAAATTAgucccaATCTCC | 73 |
| For-2 | AAAAGAGTACCCGTGCCATCG | 74 |
| For-2 | AAAAGAGTACCCGTxCCATCG | 75 |
| For-2 | AAAAGAGTACCCGxxCCATCG | 76 |
| For-2 | AAAAGAGTACCCGyyCCATCG | 77 |
| For-2 | AAAAGAGTAcccgugCCATCG | 78 |
| For-3 | ATGGGTGTAAGCAGGCTCCT | 79 |
| For-3 | ATGGGTGTAAGCAxGCTCCT | 80 |
| For-3 | ATGGGTGTAAGCxxGCTCCT | 81 |
| For-3 | ATGGGTGTAAGCyyGCTCCT | 82 |
| For-3 | ATGGGTGTaagcagGCTCCT | 83 |
| For-4 | ACATCCACCATCCATCTCCTTG | 84 |
| For-4 | ACATCCACCATCCATxTCCTTG | 85 |

TABLE 5-continued

| Binding Site | Test Oligonucleotide Primers | SEQ ID NO |
|---|---|---|
| For-4 | ACATCCACCATCCAxxTCCTTG | 86 |
| For-4 | ACATCCACCATCCAyyTCCTTG | 87 |
| For-4 | ACATCCACC**AuccaucTCCTTG | 88 |
| Rev-1 | CCACAACACGTGGGAATTCAAG | 89 |
| Rev-2 | ACTGTAATGAGAACAGGATGGGATTC | 90 |

In this example, PCR reactions were carried out with each forward primer, For-0 through For-4, along with a reverse primer, Rev-2. Each gave products of the expected size and amounts. The following polynomial amplification reactions were also carried out:

For-4+Rev-2
For-3+For-4+Rev-2
For-2+For-3+For-4+Rev-2
For-1+For-2+For-3+For-4+Rev-2
For-0+For-1+For-2+For-3+For-4+Rev-2

Each of the modified oligonucleotides set forth above was used in these reactions. Where multiple "For" primers were used, the modifications in each "For" primer were the same. For example, with the For-3, For-4, Rev-2 reaction both the For-3 and For-4 oligonucleotides contained 2'-O-methyl modifications (SEQ ID NOS: 83 and 88) in one reaction. In another reaction, they both contained nitroindole modifications (SEQ ID NOS: 82 and 87).

No products from the polynomial amplification reactions on genomic DNA were visible in gels with fewer than 50 amplification cycles. Faint products of the expected size were visible at 50 cycles. Clearly distinguishable product was only seen when reactions were with oligonucleotide primers containing a single C3 substitution or two nitroindole modified primers. The corresponding PCR reactions gave abundant product in every case.

This example demonstrates that all chemical modifications set forth in this example render primers non-replicable in amplification reactions. The modification consisting of two adjacent 3 carbon spacers and multiple 2'-O-methyl derivatized modification of oligonucleotide primers were more effective at blocking replication. Nevertheless, under the conditions disclosed in this example the polynomial amplification reactions were inefficient.

EXAMPLE 2

This example demonstrates the optimization of polynomial amplification reaction.

Polynomial amplification reaction mixtures had the following compositions:

Polyamp Reaction Mixture Ingredients 10 mM TrisCl, pH 8.3
50 mM KCl
5 mM $MgCl_2$
1 × $10^6$ copies Rat CP gene target DNA
200 µM dNTPs (50 µM each)
200 nM (10 pmoles) forward (modified) primer oligonucleotide -continued Polyamp Reaction Mixture
Ingredients 200 nM (10 pmoles) second (nested) forward primer oligonucleotide (optional)
200 nM (10 pmoles) reverse primer oligonucleotide
2.5 units Amplitaq Gold ® DNA polymerase (Applied Biosystems Inc., Foster City, CA)
50 µl final volume Reactions were conducted in a PTC-200 Peltier Thermal Cycler (MJ Research, Waltham, Mass.). Cycling conditions were: 95° C. for 15 min followed by 10, 20, 30, 40, or 50 cycles of a 3-step cycle with 95° C. for 15 sec, 50° C. for 30 sec, and 72° C. for 30 sec, followed by incubation at 72° C. for 3 min. After the amplifications were complete, the reactions were diluted to 100 µl with water. Annealing temperatures of 50° C. were typically used when oligonucleotide primers contained chemical modifications that adversely affected primer stability (Tm).

Three types of reactions were performed. These include PCR amplification, 2-primer polynomial amplification, and 3-primer "nested" polynomial amplification. PCR reactions employed the unmodified primers for the For-1 binding site shown below in Table 1. The 2-primer polynomial amplifications used a modified primers for the For-1 site and the unmodified primer for the Rev-1 site. The 3-primer nested polynomial amplifications used modified primers for the For-1 and For-2 sites, and the unmodified primer for the Rev-1 site.

To measure the amount of product produced from these reactions a PCR reaction was carried out directly on the diluted amplification product. The primers used in the PCR assay were internal unmodified primers (SEQ ID NOS: 26, 29 and 30). The oligonucleotide corresponding to SEQ ID NO: 30 was a dual-labeled fluorescence-quenched probe (Livak et al. PCR Methods Appl. 4:357-62.1995). The probe has a 6-carboxyfluorescein (6-Fam) label at its 5' end and a Black-Hole™ Quencher-1 (BH1) at its 3' end. The primers for the PCR assay were chosen to have central locations in the Rat CP gene target so that amplicons from the polynomial amplification reactions could be measured. The test system is shown below in Table 6.

A 1 µl aliquot of each amplification reaction (1% of the reaction) was used as the target source in the PCR assay. The PCR amplification was done using the Invitrogen Platinum Supermix-UDG (Carlsbad, Calif.) according to the manufacturer's directions. Reactions mixtures were composed of the ingredients set forth below in Table 7:

TABLE 7

PCR Reaction Mixture
Ingredients 20 mM TrisCl pH 8.4
50 mM KCl
3 mM $MgCl_2$
200 µM each dATP, dGTP, and dCTP
400 µM dUTP
0.5 units Uracil-DNA-N-deglycosylase
1 unit Taq DNA polymerase
50 nM Reference Dye
200 nM Primer For-3 (SEQ ID NO: 26)
200 nM Primer Rev-3 (SEQ ID NO: 29)
200 nM Probe (SEQ ID NO: 30)
1 µL Target DNA from amplification reactions or standards PCR quantitation assays were carried out with either an ABI-7700, ABI-7000, or BioRad iCycler. Pilot studies demonstrated that purification of reaction products from the polynomial amplification was not necessary and that the product reaction mixture could be added directly to the PCR reaction for amplicon quantitation.

Cycling conditions employed were: 50° C. for 2 min and 95° C. for 10 min followed by 30 cycles of 2-step PCR with 95° C. for 15 sec and 60° C. for 1 min. Control reactions were run with each experiment using known dilutions of the Rat CP gene target plasmid to establish a standard curve for quantitation including $1\times10^2$, $1\times10^4$, $1\times10^6$, and $1\times10^8$ target molecules. All data points were performed in triplicate. All PolyAmp test amplification reactions started with $1\times10^6$ molecules of input target DNA. Therefore, a 1 µl aliquot (1/100, after dilution to 100 volume) was transferred to the real-time PCR assay, resulting in a baseline transfer of $1\times10^4$ molecules of target. Any increase above $1\times10^4$ molecules was considered as the result of amplification in the polynomial amplification reaction.

To optimize the magnesium concentration and annealing temperature in the amplification reactions, primers at the For-1 site containing the C3 spacer (1,3-propanediol, designated with an "x"), the nitroindole spacer (designated with a "y") and the d-Spacer (1,4-anhydro-2-deoxy-D-ribitol, designated with a "d") blocking groups were prepared and used as single or double insertions. These primers were used with a single reverse primer Rev-1. The magnesium concentration dependence of the reactions was tested using 1.5, 2, 3 and 5

TABLE 6

```
                                  Oligonucleotide Primer Binding Sites
        For-0                                    For-1                           For-2
GGATCCTCTAGATGCATGCTCGAGTAATACGACTCACTATAGACATGGTCAACCCCACCGTGTTCTTCGACAT
>>>>>>>>>>>>>>>>>>>>>        >>>>>>>>>>>>>>>>>>>>>>> >>>>>>>>>>>>>>>>>>>>

SEQ ID NO: 26         SEQ ID NO: 30              SEQ ID NO: 29
ACGGCTGATGGCGAGCCCTTGGGTCGCGTCTGCTTCGAGCTGTTTGCAGACAAAGTTCCAAAGACAGCAGAAAAC
    >>>>>>>>>>>>>>>>>>>  *********************  <<<<<<<<<<<<<<<<<<<<<<<<

Rev-2                                   Rev-1
TTTCGTGCTCTGAGCACTGGGGAGAAAGGATTTGGCTATAAGATGATACACTCCGACATAACGTGGATCC
              <<<<<<<<<<<<<<<<<<<<              <<<<<<<<<<<<<<<<<<<<
``` mM magnesium concentrations. Annealing temperatures were tested at about 50, 54, and 58° C.

The following oligonucleotides (shown in Table 8) were used individually with the Rev-1 primer:

TABLE 8

| Binding Site | Test Oligonucleotide Primers | SEQ ID NO |
|---|---|---|
| For-1 | ACGACTCACTATAGACATGGTCAAC | 12 |
| For-1 | ACGACTCACTATAGACATyGTCAAC | 13 |
| For-1 | ACGACTCACTATAGACAyyGTCAAC | 14 |
| For-1 | ACGACTCACTATAGACATxGTCAAC | 15 |
| For-1 | ACGACTCACTATAGACAxxGTCAAC | 16 |
| For-2 | CCACCGTGTTCTTdGACATC | 36 |
| For-2 | CCACCGTGTTCTddGACATC | 37 |
| Rev-1 | GATCCACGTTATGTCGGAGTG | 27 |

Results from the study are shown below in Table 9:

TABLE 9

| | $Mg^{2+}$ Concentration | | | |
|---|---|---|---|---|
| SEQ ID NO | 1.5 | 2 | 3 | 5 |
| $12^1$ | $10^4$ | $3 \times 10^6$ | $10^7$ | $10^7$ |
| 13 | $3 \times 10^4$ | $5 \times 10^5$ | $10^7$ | $10^7$ |
| 14 | $3 \times 10^4$ | $2 \times 10^5$ | $10^7$ | $10^7$ |
| $15^2$ | | $3 \times 10^6$ | $3 \times 10^7$ | $3 \times 10^7$ |
| $16^2$ | | $3 \times 10^5$ | $3 \times 10^6$ | $1 \times 10^7$ |
| $36^2$ | | $1 \times 10^6$ | $2 \times 10^7$ | $3 \times 10^7$ |
| $37^2$ | | $2 \times 10^5$ | $2 \times 10^6$ | $6 \times 10^6$ |

[1]Data for 10 temperature cycles
[2]Data obtained using a 50° C. annealing temperature These experiments demonstrated that for the indicated primers, 5 mM magnesium consistently gave the greatest amount of amplified product. This also was the optimal concentration when reactions were carried out with higher annealing temperatures of 54° C. and 58° C.

EXAMPLE 3

This example evaluates the annealing temperature of the polynomial amplification reaction method with various modified oligonucleotide primers.

Polynomial amplification reactions were carried out as described in Example 2 using 5 mM $MgCl_2$ and varying the annealing temperatures in the temperature cycling method. Annealing temperatures of 50° C., 54° C., and 58° C. were compared. The following oligonucleotide primers (shown in Table 10) were investigated:

TABLE 10

| | Oligonucleotide Primer Sequences | |
|---|---|---|
| | ACGACTCACTATAGACATGGTCAAC | SEQ ID NO: 12 |
| 1xNI: | ACGACTCACTATAGACATyGTCAAC | SEQ ID NO: 13 |
| 2xNI: | ACGACTCACTATAGACAyyGTCAAC | SEQ ID NO: 14 |
| 1xC3: | ACGACTCACTATAGACATxGTCAAC | SEQ ID NO: 15 |
| 2xC3: | ACGACTCACTATAGACAxxGTCAAC | SEQ ID NO: 16 |
| 1x-dS: | CCACCGTGTTCTTdGACATC | SEQ ID NO: 36 |
| 2x-dS: | CCACCGTGTTCTddGACATC | SEQ ID NO: 37 |
| 2'-O-methyl | GGATCCTCTAgaugcaTGCTCG | SEQ ID NO: 38 |
| | GATCCACGTTATGTCGGAGTG | SEQ ID NO: 27 |

Unmodified primers in amplification reactions were found to be optimal from both quantitative (Taqman) and purity (gel) aspects when the process utilizes annealing temperatures of 58-60° C. The optimal annealing temperature varied with the modification employed in the primers used for polynomial amplification. The C3 and d-spacer-containing oligonucleotides (SEQ ID NOS: 15, 16, 36, and 37) gave the highest yields when an annealing temperature of 50° C. was used. This temperature was superior to 54° C. and 54° C. was far superior to the amplification with annealing at 58° C. With respect to the nitroindole-modified oligonucleotides (SEQ ID NOS: 13 and 14) the amplifications obtained with annealing temperatures of 50° C. and 54° C. were about the same and both temperatures were far superior to 58° C. The oligonucleotide (SEQ ID NO: 39) containing the 2'-O-methyl groups worked better with an annealing temperature of 55° C. than with annealing temperatures of 50° C. or 58° C.

Similar experiments were carried out to optimize the dNTP, oligonucleotide and polymerase concentrations. Concentrations of about 200 µM for each dNTP and about 2.5 units polymerase per 50 µL reaction for Amplitaq Gold® DNA Polymerase were found to be optimal.

With regard to oligonucleotide primer concentrations, the relative concentration of each primer in a nested primer set was varied to determine if increasing any single primer was more important than others. The reaction yields were not significantly improved by increasing the concentrations of any individual primer. However, about a 10-fold increase in yield was obtained when the concentrations of all primers were increased by 10-fold to about 2 µM. The oligonucleotide primer concentrations in the tests ranged between 0.2 to 3 µM.

In summary, the optimal polynomial amplification reaction conditions are shown below in Table 11:

TABLE 11

Optimized Polynomial Amplification Reaction Mixture 10 mM Tris pH 8.3
50 mM KCl
5.0 mM $MgCl_2$
800 µM dNTPs (200 µM each)
Target DNA
2.0 µM (100 pmoles) forward (modified) primer oligonucleotide
2.0 µM (100 pmoles) additional (nested) forward (modified) primer oligonucleotides
2.0 µM (100 pmoles) reverse primer oligonucleotide
2.5 units Amplitaq Gold ® DNA polymerase
50 µl final volume

EXAMPLE 4

This example demonstrates that polynomial amplification occurs with a wide variety of modified oligonucleotides.

Polynomial amplification reactions were carried out with the oligonucleotide pairs set out below, the size of the amplicon generated from each pair is also shown (Table 12).

TABLE 12

| Pair | Oligonucleotide Primer Sequence | Amplicon Size |
|---|---|---|
| For-0 | GGATCCTCTAGATGCATGCTCG | 218 bp |
| Rev-1 | GATCCACGTTATGTCGGAGTG | |
| For-0 | GGATCCTCTAGATGCATGCTCG | 183 bp |
| Rev-2 | CCAAATCCTTTCTCCCCAGTG | |
| For-1 | ACGACTCACTATAGACATGGTCAAC | 191 bp |
| Rev-1 | GATCCACGTTATGTCGGAGTG | |
| For-1 | ACGACTCACTATAGACATGGTCAAC | 156 bp |
| Rev-2 | CCAAATCCTTTCTCCCCAGTG | |
| For-2 | CCACCGTGTTCTTCGACATC | 165 bp |
| Rev-1 | GATCCACGTTATGTCGGAGTG | |
| For-2 | CCACCGTGTTCTTCGACATC | 130 bp |
| Rev-2 | CCAAATCCTTTCTCCCCAGTG | |
| For-3 | ATGGCGAGCCCTTGGG | 68 bp |
| Rev-3 | GTTTTCTGCTGTCTTTGGAACTTTG | |
| probe | Fam-CGCGTCTGCTTCGAGCTGTTTGC-BH1 | |

The modified oligonucleotides that were used in each of the pairs listed above are shown below in Table 13.

TABLE 13

| Primer Binding Site | Sequence | SEQ ID NO |
|---|---|---|
| For-0 | GGATCCTCTAGATGCATGCTCG | 39 |
| For-0 | GGATCCTCTAGATGCxTGCTCG | 40 |
| For-0 | GGATCCTCTAGATGxxTGCTCG | 41 |
| For-0 | GGATCCTCTAGATGyxTGCTCG | 42 |
| For-0 | GGATCCTCTAgaugcaTGCTCG | 43 |
| For-1 | ACGACTCACTATAGACATGGTCAAC | 12 |
| For-1 | ACGACTCACTATAGACATyGTCAAC | 13 |
| For-1 | ACGACTCACTATAGACAyyGTCAAC | 14 |
| For-1 | ACGACTCACTATAGACATxGTCAAC | 15 |
| For-1 | ACGACTCACTATAGACAxxGTCAAC | 16 |
| For-1 | ACGACTCACTATAGACAyxGTCAAC | 17 |
| For-1 | ACGACTCACTATAGACyyxGTCAAC | 18 |
| For-1 | ACGACTCACTATAgacaugGTCAAC | 44 |
| For-2 | CCACCGTGTTCTTCGACATC | 19 |
| For-2 | CCACCGTGTTCTTdGACATC | 45 |
| For-2 | CCACCGTGTTCTddGACATC | 46 |
| For-2 | CCACCGTGTTCTxxGACATC | 23 |
| For-2 | CCACCGTGTTCTyxGACATC | 24 |
| For-2 | CCACCGTGTTCyyxGACATC | 25 |

TABLE 13-continued

| Primer Binding Site | Sequence | SEQ ID NO |
|---|---|---|
| For-2 | CCACCGTGuucuucGACATC | 47 |
| Probe | Fam-CGCGTCTGCTTCGAGCTGTTTGC-BH1 | 30 |

When single modifications were incorporated into oligonucleotide primers the amplification observed was lower than in PCR at cycle numbers of less than about 40. However, when amplification was increased to about 50 cycles, all experiments done with single "For" primers having a single modification produced more amplification than would be theoretically possible for a polynomial amplification reaction. As a consequence, multiple modifications are preferred in non-replicable primers. The maximum amplification achieved in the reactions using between 10 and 30 amplification cycles was about 3000-fold.

Primers containing two modifications gave lower overall yields but were better able to maintain the polynomial amplification reaction character. The double C3 modification and or C3 modification adjacent to the nitroindole modification, gave the lowest amplicon yield of only 1% of that predicted for the true polynomial amplification reaction. The yield from double modified primers in the polynomial amplification reaction was increased by the use of multiple modified primers for one strand and a single unmodified primer for the opposing strand. The primers used were as follows (Table 14):

TABLE 14

| Primer Binding Site | Sequence | SEQ ID NO |
|---|---|---|
| For-0 | GGATCCTCTAGATGxxTGCTCG | 41 |
| For-1 | ACGACTCACTATAGACAxxGTCAAC | 16 |
| For-2 | CCACCGTGTTCTxxGACATC | 23 |
| Rev-1 | GATCCACGTTATGTCGGAGTG | 27 |

EXAMPLE 5

This example evaluates whether additional non-replicable primers can be used to increase the amplicon yield in polynomial amplification reactions.

In the reactions in this example additional non-replicable primers were added to the reaction mixtures including chemically modified primers For-00, For-000, and For-0000. In addition, the amplification reaction mixture was modified in accordance with Example 3. The amplification reactions included more nucleotide triphosphates, primer, and input target DNA. The reaction mixtures were as follows (Table 15):

TABLE 15

Polyamp Reaction Mixture Ingredients 10 mM Tris pH 8.3
50 mM KCl
5.0 mM MgCl$_2$
200 µM each dNTP
100 ng human genomic DNA

TABLE 15-continued

Polyamp Reaction Mixture
Ingredients 2.0 μM (100 pmoles) each forward (modified) primer oligonucleotide
2.0 μM (100 pmoles) reverse primer
2.5 units Amplitaq Gold ® DNA polymerase
50 μl final volume Cycling conditions employed were: 95° C. for 15 min followed by 30, 40, or 50 cycles of a 3-step cycle with 95° C. for 30 sec, 55° C. (or 60° C.) for 60 sec, and 72° C. for 30 sec, followed by incubation at 72° C. for 3 min. After the amplifications were completed, the reaction mixtures were diluted to 100 μl volume with water. Reaction products were subjected to PAGE and visualized by staining as described above. Products were also subjected to a real-time PCR assay to determine the amount of product produced in the polyamp assay.

The primer samples tested in this example include each unmodified "For" primer with the Rev-2 primer in a PCR reaction. For polynomial amplification reactions the primer sets tested were as follows:

Samples Tested:
Reaction 1: For-4+Rev-2
Reaction 2: For-3+For-4+Rev-2
Reaction 3: For-2+For-3+For-4+Rev-2
Reaction 4: For-1+For-2+For-3+For-4+Rev-2
Reaction 5: For-0+For-1+For-2+For-3+For-4+Rev-2
Reaction 6: For-00+For-0+For-1+For-2+For-3+For-4+Rev-2
Reaction 7: For-000+For-0+For-1+For-2+For-3+For-4+Rev-2
Reaction 8: For-000+For-00+For-0+For-1+For-2+For-3+For-4+Rev-2
Reaction 9: For-0000+For-000+For-0+For-1+For-2+For-3+For-4+Rev-2
Reaction 10: For-0000+For-000+For-00+For-0+For-1+For-2+For-3+For-4+Rev-2

The polynomial amplification reaction was carried out through 40 cycles and the results from of these reactions done twice (Expt. 1 and Expt. 2) are set forth below (Table 16):

TABLE 16

| | Amplicon yield | |
|---|---|---|
| | Expt. 1 | Expt. 2 |
| Reaction 1 | $7 \times 10^7$ | $3 \times 10^7$ |
| Reaction 2 | $6 \times 10^8$ | $5 \times 10^8$ |
| Reaction 3 | $2 \times 10^{10}$ | $2 \times 10^{10}$ |
| Reaction 4 | $9 \times 10^{10}$ | $1 \times 10^{11}$ |
| Reaction 5 | $2 \times 10^{11}$ | $2 \times 10^{11}$ |
| Reaction 6 | $1 \times 10^9$ | |
| Reaction 7 | | $2 \times 10^{11}$ |
| Reaction 8 | $4 \times 10^{10}$ | |
| Reaction 9 | | $2 \times 10^{11}$ |
| Reaction 10 | $1 \times 10^{10}$ | |

Comparison of the amplicon yield from Reaction 6 with Reaction 7 and comparison of the amplicon yield from Reaction 8 with Reaction 9 demonstrated that, at least in the presence of multiple primers, the primer For-00 significantly reduced the amplicon yield. Thus, it was determined that the primer For-00 should not be included in further amplification mixtures, such as Reaction 10.

This example shows that in this test system amplification increases with each added oligonucleotide primer until about four or five non-replicable primers are present in a reaction. The system then appears to become saturated with non-replicable primers and no significant increase in amplification is seen after about 5 non-replicable primers were added.

The experiment was repeated with the exception that a 60° C. annealing temperature was used in the temperature cycling program. A similar plateau was reached although the yields were approximately 10-fold higher in each reaction.

EXAMPLE 6

This example evaluates the extent to which the products generated in the polynomial amplification reaction reduce the problem of obtaining false-positive results in subsequent reactions due to carry-over contamination.

Reaction products from reactions 1-5 in Example 5 were diluted and used as the source of target DNA in a second round of polynomial amplification reactions. The product reaction mixtures from the second round amplifications were then subjected to the PCR assay described above to determine the level of amplification in the second reaction. As a control, a 40-cycle PCR was done on the reaction products from Reaction 5 using oligonucleotides SEQ ID NO: 84 and 90.

When used as target DNA, the products from polynomial amplification reactions produced about 10,000-fold less amplification than corresponding amounts of genomic DNA. When used as target DNA in PCR reactions the same products were efficiently amplified. This reduction in amplification is called the sterilization number (i.e., the sterilization number is 10,000).

EXAMPLE 7

This example provides another evaluation of the extent to which products of the polynomial amplification reaction reduce false-positive results in subsequent reactions caused by carry-over contamination.

A series of polynomial amplifications were carried out under the conditions set forth in Example 5. The primer sets for the reactions and the amount of product produced in each reaction as determined with the NOD2 PCR assay described in Example 5 are shown below (Table 17).

TABLE 17

| Oligonucleotides | Approximate Quantity of Product |
|---|---|
| Reaction 1  SEQ ID NOS: 90, 88 | $2 \times 10^6$ |
| Reaction 2  SEQ ID NOS: 90, 88, 83 | $1 \times 10^8$ |
| Reaction 3  SEQ ID NOS: 90, 88, 83, 78 | $3 \times 10^9$ |
| Reaction 4  SEQ ID NOS: 90, 88, 83, 78, 73 | $3 \times 10^{10}$ |
| Reaction 5  SEQ ID NOS: 90, 88, 83, 78, 73, 58 | $3 \times 10^{10}$ |
| Reaction 6  SEQ ID NOS: 90, 88, 83, 78, 73, 58, 53 | $3 \times 10^{10}$ |

To determine the extent to which polynomial amplification reaction products are capable of serving as templates in subsequent amplification reactions, the product reaction mixture from Reaction 5 was diluted to 100 μl and added as target DNA to a series of test polynomial amplification reactions and to a series of test PCR reactions. About $1 \times 10^4$ copies of target DNA was added to each secondary amplification reaction. After completion of the second polynomial amplification reaction, the amount of product in each reaction mixture was determined using the quantitative NOD2 PCR assay.

The test PCR reactions each separately included oligonucleotide SEQ ID NO: 90 and each of the possible "For"

primers from the series of unmodified "For" primers. The "For" primers included SEQ ID NOS: 49, 54, 59, 64, 69, 74, 79 and 84.

The test PCR reactions gave an abundant amount of product in each reaction. The amount of product ranged from about $1\times10^{11}$ with SEQ ID NO: 84 and steadily decreased to about $7\times10^9$ with the SEQ ID NO: 49 which was the primer farthest from the center of the amplicon produced by the polynomial amplification and therefore the least abundant, in all likelihood.

In contrast, the test polynomial amplification reactions provided limited amplification of Reaction 6 target DNA, demonstrating that polynomial amplification products are poor targets for additional rounds of polynomial amplification. The results from the test PCR amplification and the test polynomial amplification reaction are shown below (Table 18):

TABLE 18

|  | Genomic NOD2 Target Amplicon Yield | Reaction 5 Target Amplicon Yield |
| --- | --- | --- |
| Reaction 1 | $2 \times 10^6$ | $1 \times 10^5$ |
| Reaction 2 | $1 \times 10^8$ | $3 \times 10^6$ |
| Reaction 3 | $3 \times 10^9$ | $1 \times 10^7$ |
| Reaction 4 | $4 \times 10^{10}$ | $2 \times 10^7$ |
| Reaction 5 | $6 \times 10^{10}$ | $1 \times 10^7$ |
| Reaction 6 | $8 \times 10^{10}$ | $1 \times 10^7$ |

Polynomial amplification reaction products are poor substrates for additional rounds of polynomial amplification. By comparing the observed yield from the polynomial amplification reaction above using target DNA from the polynomial amplification (Reaction 6 above) versus genomic target DNA, a number identified for purposes of this invention as "effective sterilization" can be obtained. In the preferred range of about four non-replicable primers, the effective sterilization is Over about $1\times10^3$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The terms "at least" and "or more" have identical meanings when referring to particular values. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for amplifying a nucleotide sequence of interest in a nucleic acid polymer, which method comprises treating a reaction mixture that comprises the nucleic acid polymer, a replicable primer and at least a first non-replicable primer having a cleavable element that is cleavable by a ribonuclease under conditions such that:
   (i) a first extension product is produced from the first non-replicable primer using the nucleic acid polymer as a template, and
   (ii) a second extension product is produced from the replicable primer using the first extension product as a template, wherein the second extension product is unable to serve as a template for extension of the first non-replicable primer.

2. The method of claim 1, in which the cleavable element comprises one or more ribonucleotides incorporated into the first non-replicable primer.

3. The method of claim 2, in which the cleavable element comprises a single ribonucleotide.

4. The method of claim 2, in which the one or more ribonucleotides are incorporated at a 3'-terminus of the first non-replicable primer.

5. The method of claim 1, in which the ribonuclease is a mammalian RNase A.

6. The method of claim 1, in which the ribonuclease is an *Aspergillus* RNase T1.

7. The method of claim 1, in which the ribonuclease is an RNaseH.

8. The method of claim 1, in which the RNase H is a human RNase H.

9. The method of claim 1, further comprising steps of:
   (a) separating the first and second extension products from the templates, and
   (b) treating the resulting mixture under conditions such that additional first and second extension products are produced.

10. The method of claim 9, wherein the steps of separating extension products and treating the resulting mixture are repeated a plurality of times.

11. The method of claim 9, wherein the steps of separating extension products and treating the resulting mixture are repeated from about 20 to about 60 times.

12. The method of claim 1 in which the reaction mixture additionally comprises a second non-replicable primer.

13. The method of claim 12, in which:
   (iii) a third extension product is produced from the second non-replicable primer, using the nucleic acid polymer as a template; and
   (iv) a fourth extension product is produced from the replicable primer, using the third extension product as a template, wherein the fourth extension product is unable to serve as a template for extension of the second non-replicable primer.

14. The method of claim 12, in which the reaction mixture comprises a third non-replicable primer that is capable of hybridizing to the nucleic acid polymer.

15. The method of claim 1, in which the reaction mixture comprises from one to five non-replicable primers that are capable of hybridizing to the nucleic acid polymer.

16. The method of claim 1, in which the replicable primer is detectably labeled.

17. The method of claim 1 in which the nucleic acid sequence of interest is first amplified by a polymerase chain reaction (PCR).

18. The method of claim 17, in which about 10 to about 20 cycles of PCR are performed.

19. A method for amplifying a nucleotide sequence of interest in a nucleic acid polymer, which method comprises treating a reaction mixture that comprises the nucleic acid polymer and a primer set having at least a first non-replicable primer, a second non-replicable primer and a replicable primer under conditions such that:
  (i) a first extension product is produced from the first non-replicable primer using the nucleic acid polymer as a template;
  (ii) a second extension product is produced from the replicable primer using the first extension product as a template; and
  (iii) a third extension product is produced from the second non-replicable primer using the second extension product as a template;
  (iv) a fourth extension product is produced from the replicable primer using the third extension product as a template, wherein the second extension product is unable to serve as a template for extension of the first non-replicable primer, and the fourth extension product is unable to serve as a template for extension of the second non-replicable primer.

20. The method of claim 19, in which the reaction mixture comprises a third non-replicable primer that is capable of hybridizing to the nucleic acid polymer.

21. The method of claim 20, in which the reaction mixture comprises a fourth non-replicable primer that is capable of hybridizing to the nucleic acid polymer.

22. The method of claim 19, in which the reaction mixture comprises from two to five non-replicable primers that are capable of hybridizing to the nucleic acid polymer.

23. The method of claim 19, in which at least one of the first and second non-replicable primers comprises a 2'-O-alkyl ribose base.

24. The method of claim 23, in which at least one of the first and second non-replicable primers comprises four or more adjacent 2'-O-alkyl riboses bases.

25. The method of claim 23, in which the 2'-O-alkyl ribose base is a 2'-O-methyl ribose base.

26. The method of claim 19, in which at least one of the first and second non-replicable primers comprises an internucleotide extender.

27. The method of claim 26, in which the internucleotide extender comprises a 1,3-propanediol.

28. The method of claim 19, in which at least one of the first and second non-replicable primers comprises a cleavable element.

29. The method of claim 28, in which the cleavable element comprises one or more ribonucleotides incorporated into the non-replicable primer.

30. The method of claim 29, in which the cleavable element comprises a single ribonucleotide.

31. The method of claim 29, in which the one or more ribonucleotides are incorporated at a 3'-terminus of the first non-replicable primer.

32. The method of claim 28, in which the cleavable element is cleavable by a ribonuclease.

33. The method of claim 32, in which the ribonuclease is a mammalian RNase A.

34. The method of claim 32, in which the ribonuclease is an *Aspergillus* RNase H.

35. The method of claim 32, in which the ribonuclease is RNaseH.

36. The method of claim 35, in which the RNase H is a human RNase H.

37. The method of claim 19, in which the nucleic acid polymer is genomic DNA.

38. The method of claim 19 in which the nucleic acid polymer is cDNA.

39. The method of claim 19, in which the replicable primer is detectably labeled.

40. The method of claim 19, in which the nucleic acid sequence of interest is first amplified by a polymerase chain reaction (PCR).

41. The method of claim 40, in which about 10 to about 20 cycles of PCR are performed.

* * * * *